(12) United States Patent
Tindall

(10) Patent No.: US 12,138,492 B2
(45) Date of Patent: Nov. 12, 2024

(54) PERSONAL PROTECTIVE FACEMASK SYSTEM

(71) Applicant: Tim Tindall, Holden, ME (US)

(72) Inventor: Tim Tindall, Holden, ME (US)

( * ) Notice: Subject to any disclaimer, the term of this patent is extended or adjusted under 35 U.S.C. 154(b) by 427 days.

(21) Appl. No.: 17/516,040

(22) Filed: Nov. 1, 2021

(65) Prior Publication Data

US 2022/0161065 A1 May 26, 2022

Related U.S. Application Data

(60) Provisional application No. 63/116,332, filed on Nov. 20, 2020.

(51) Int. Cl.
*A62B 18/02* (2006.01)
*A61F 9/02* (2006.01)
*A61F 9/06* (2006.01)
*A62B 7/10* (2006.01)
*A62B 18/08* (2006.01)

(52) U.S. Cl.
CPC ............ *A62B 18/02* (2013.01); *A62B 7/10* (2013.01); *A62B 18/084* (2013.01); *A61F 9/028* (2013.01); *A61F 9/068* (2013.01)

(58) Field of Classification Search
CPC .... A62B 7/00; A62B 7/10; A62B 7/12; A62B 18/00; A62B 18/006; A62B 18/02; A62B 18/025; A62B 18/084; A41D 13/11; A41D 13/1184; A61F 9/028; A61F 9/068
See application file for complete search history.

(56) References Cited

U.S. PATENT DOCUMENTS

| | | | | |
|---|---|---|---|---|
| 5,009,225 A | * | 4/1991 | Vrabel ............... | A62B 18/006 128/202.19 |
| 5,704,073 A | * | 1/1998 | Sword ............... | A41D 13/1176 2/427 |
| 10,463,091 B2 | * | 11/2019 | Bourque ............. | A41D 13/11 |
| 2018/0078798 A1 | * | 3/2018 | Fabian ............... | A62B 18/10 |

* cited by examiner

*Primary Examiner* — Keri J Nelson
(74) *Attorney, Agent, or Firm* — Brennan, Manna & Diamond, LLC

(57) ABSTRACT

The present invention relates to a multifunctional transparent facemask system having a transparent facemask that seals over the nose, jawbone, and neck of a wearer to provide clean air for inhalation. The system filters out harmful contaminates from exhaled air before the exhaled air is released into the environment. The facemask system includes a removable visor to be disposed in front of the eyes of the wearer to prohibit drying of the eyes and preventing pathogens from entering therein. The system includes an air pump for providing fresh air to the facemask, an air filter for filtering out harmful contaminates from exhaled air, an inlet pipe for fresh air flow into the facemask, an outlet pipe for flowing exhaled air out from the facemask, and a small air tube for providing fresh air to the visor. The facemask includes a microphone and a speaker for providing effective communication, and LEDs for illumination.

20 Claims, 4 Drawing Sheets

PERSONAL PROTECTIVE FACEMASK SYSTEM

CROSS-REFERENCE TO RELATED APPLICATION

The present application claims priority to, and the benefit of, U.S. Provisional Application No. 63/116,332, which was filed on Nov. 20, 2020 and is incorporated herein by reference in its entirety.

FIELD OF THE INVENTION

The present invention relates generally to the field of protective facemasks. More specifically, the present invention relates to a personal protective facemask system that covers the nasal and oral passage, while sealing the nose, jawbone and neck area to properly secure the mask over the face of the users. The comprehensive protective facemask comprises an air filter tube connected on each side of the mask, which is connected to an air filtering unit to provide clean air for inhalation, and to filter out harmful contaminates from exhaled air. The protective facemask comprises a microphone and speakers to facilitate clear crisp voice transmission while wearing the mask. Additionally, the protective facemask is attached to a visor with an air dam system to keep out harmful vapors, pathogens, and irritants. Accordingly, the present disclosure makes specific reference thereto. Nonetheless, it is to be appreciated that aspects of the present invention are also equally applicable to other like applications, devices, and methods of manufacture.

BACKGROUND OF THE INVENTION

By way of background, in the times of pandemics, there is a huge risk of spread of infectious diseases around the world. In history, pandemics have not only affected a substantial number of individuals but have also taken a toll on life of millions of individuals. A number of pandemics such as smallpox, tuberculosis, Plague, Spanish Flu and others have affected individuals in the past. Also, pandemics like HIV/AIDS and Coronavirus diseases (i.e. COVID-19) exist currently that cause the exponential spread of viruses, bacteria or pathogens, thereby causing the spread of infectious diseases among individuals.

Generally, to prevent the spread of infectious diseases, individuals are often advised to follow social distancing guidelines, maintain personal hygiene, wear protective facemasks and more. To protect oneself against transmission of germs and other harmful pathogens present in the environment and that are transmissible through air intake, individuals usually prefer wearing facemasks, as they act as a barrier between the oral and nasal passage of the user and the outer environment, and protect the users from transmission of germs, viruses, bacteria and other harmful pathogens. The use of a facemask avoids contact between those who are infected with any virus, bacteria or the like, and those who are not, so as to stop or slow down the rate and extent of disease transmission.

Typically, a facemask comprises a layer of protective fabric designed to cover the nose and mouth region. The mask is connected to ear loops to allow a user to easily wear the facemask. The standard facemasks, heretofore known, may not be able to properly seal the protective fabric over the wearer's face, and may allow germs, bacteria, and other harmful pathogens to travel inside the mask and transmit through the nasal and oral passages to cause infectious disease to the wearer. Additionally, while standard fabric masks can slow the spread of some pathogens, they may be ineffective at preventing transmission of viruses and other smaller-sized pathogens.

Further, the ear loops of the standard masks may include sharp string-like construction that can cause discomfort to the wearer. Individuals may be forced to remove the mask due to discomfort caused by the conventional ear loops in protective facemasks. Additionally, the standard facemask prohibits the transmission of some germs, bacteria and other harmful pathogens through the oral and nasal passages. However, the eyes of the wearer are exposed and therefore are not protected from both direct projectiles and contaminates suspended in the air. Some individuals may use face shields in combination with the facemasks, however it may be difficult to handle both a face shield and a facemask together, and the wearer may become quite uncomfortable.

Furthermore, conventional facemasks are non-transparent, and therefore they do not allow facial expressions to be seen. Also, while wearing facemasks, the voice of the wearer may not be properly transmitted to other individuals and the wearer may be unheard by others. Due to these issues, individuals may fail to effectively communicate with others while wearing standard facemasks.

In addition to the above-mentioned issues, some masks and forced air helmets can cause vision problems by fogging up glasses. The wearer may be required to constantly clear the fogged-up glasses to get a clear view through the glasses. However, it can be dangerous for the wearer to constantly clear fogged-up glasses while driving a vehicle.

Therefore, there exists a long felt need in the art for a protective facemask that provides effective protection against transmission of germs and other harmful pathogens and therefore prevents the wearer from spread of infectious diseases. There is also a long felt need in the art for a protective facemask that properly seals the mask over the wearer's face, and prevents any germs from travelling into and out of the mask. Additionally, there is a long felt need in the art for a facemask that provides an enhanced mask-securing mechanism that is comfortable for the wearer and enables the wearer to wear the facemask for a long period of time. Moreover, there is a long felt need in the art for a facemask that protects the eyes of the wearer from direct projectiles and contaminants suspended in the air. Further, there is a long felt need in the art for a facemask that eliminates the need to wear facemasks and face shields together. Furthermore, there is a long felt need in the art for a facemask that enables the expressions of the wearer to be clearly visible to others. There is a long felt need in the art for a facemask that enables the wearer to be properly heard by others in order to have an effective communication with others. There is a long felt need in the art for a facemask that prevents fogging up of glasses and eliminates the need to constantly clear the fogged-up glasses. Finally, there is a long felt need in the art for a comprehensive facemask that maintains a high level of security for the wearer when in public places with others, while effectively preventing the inhalation and spread of germs, viruses and bacteria.

The subject matter disclosed and claimed herein, in one embodiment thereof, comprises a transparent facemask system for providing filtered air to a wearer and effectively reduce inhaling harmful airborne pathogens. More specifically, the facemask system comprises a transparent facemask configured to cover the nose, mouth, jawline, and a portion of a neck of a wearer. The mask further comprises a removable transparent visor for covering the eyes of the wearer. The transparent facemask is secured behind the neck of the wearer using a fastener enabling the facemask to seal over or cover the nose, mouth, jawline and a portion of the neck. The facemask comprises an inlet pipe and an outlet pipe coupled to an air filtering system, wherein the inlet pipe enables fresh air to enter into the facemask, and the outlet pipe enables exhaled air to flow through a filter and out from the facemask. Additionally, the mask includes a speaker and a microphone to allow the wearer to effectively communicate with others.

In this manner, the novel personal protective facemask system of the present invention accomplishes all of the forgoing objectives, and provides a relatively safe, easy and convenient solution to prevent the transmission of germs, bacteria and other harmful pathogens, and protect the wearer against spread of infectious diseases and other airborne particles. The personal protective facemask system of the present invention is also user-friendly, as it ensures the user is able to effectively communicate with others while wearing the facemask. The facemask is comfortable to use, and ensures the wearer is able to wear the mask for a long period of time.

SUMMARY OF THE INVENTION

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a transparent facemask system for providing filtered air to a wearer and effectively reducing inhalation of harmful airborne pathogens. More specifically, the facemask system further comprises: a transparent facemask configured to cover the nose, mouth, jawline and a portion of a neck of a wearer; a removable transparent visor for covering the eyes of the wearer; the transparent facemask is secured behind the neck of the wearer using a fastener enabling the facemask to seal over or cover the nose, mouth, jawline and at least a portion of the neck; the transparent visor includes a perforated tube around the periphery; the facemask being associated with an inlet pipe and an outlet pipe; the inlet pipe enables fresh air to enter into the facemask; the outlet pipe enables exhaled air to flow out from the facemask; the inlet pipe and the outlet pipe are coupled to an air pump for pumping air into and out of the facemask; the inlet pipe and the outlet pipe are coupled to an air filter for filtering air before pumping into the facemask and releasing exhaled air through a filter to the environment; a small air tube connected to the inlet pipe and the perforated tube; and, the small air tube receives fresh air from the inlet pipe and transmits same to the perforated tube creating an air dam system within the visor to direct air away from the eyes and to prohibit eye dehydration. The air filter and the air pump receive power from a built-in battery.

In yet another embodiment of the present invention, a plurality of LEDs can be disposed along a top edge of the transparent facemask for indicating working status of the air pump and the air filter. The LEDs can illuminate in a specific color, such as red, to indicate malfunctioning of the air pump and the air filter, and can illuminate in another specific color to indicate correct functioning of the air pump and the air filter.

In yet another embodiment of the present invention, a microphone is disposed on the transparent facemask to capture voice signals of the wearer, and a speaker system is disposed for amplifying the captured voice signals of the wearer of the facemask system for effective communication with other individuals.

In yet another embodiment of the present invention, the perforated tube surrounds generally around a periphery of the visor, wherein the perforations are aimed to direct air to the skin of the wearer for preventing the eyes of the wearer from drying out.

In yet another embodiment of the present invention, the inlet pipe enables unidirectional flow from the air pump to the facemask enabling fresh air to enter into the facemask, and the outlet pipe enables unidirectional flow from the facemask to the air pump, therby enabling exhaled air to exit from the facemask.

In a further embodiment of the present invention, a full-facemask system is disclosed. The full-facemask system is designed to deliver clean and filtered air to a wearer and effectively reduce the chance of inhaling harmful airborne pathogens. The full-facemask system includes: a transparent facemask defined by a top, a bottom, a left side and a right side; a rigid mask support structure defining a shape of the facemask to cover the nose, mouth, jawline and a portion of a neck of the wearer; a fastener to fasten the facemask behind the neck of the wearer to seal the facemask; a removable visor to cover the eyes of the wearer configured to connect to the top side of the facemask; an air inlet pipe extending from the facemask to an air pump for providing fresh air into the facemask for the wearer; an air outlet pipe extending from the air pump to the facemask for removing exhaled air from the facemask; the air pump is coupled to the air filter for filtering the air; and, a small air tube for providing fresh air to a perforated tube mounted around a periphery of the visor to assist with prohibiting dehydration of the eyes.

In a further embodiment of the present invention, a modified personal protective facemask system is disclosed. The modified personal protective facemask system includes: a transparent facemask; a removable transparent visor; a pair of air tubes for providing fresh air to inhale and removing exhaled air; a microphone disposed on the facemask for capturing a wearer's voice; a speaker system disposed on the facemask to amplify wearer's voice for effective communication; a plurality of LEDs; an air filter for filtering air for inhalation and cleaning exhaled air; an air pump for pumping air for inhalation and removing exhaled air; and, a battery for providing power to the air pump, air filter, microphone, speaker and LEDs. In yet another embodiment, a transparent facemask system or full-facemask system or modified personal protective facemask system of the aforementioned type can be referred to as an "Ultra-Mask".

To the accomplishment of the foregoing and related objectives, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION OF THE PRESENT INVENTION

Figure 1:
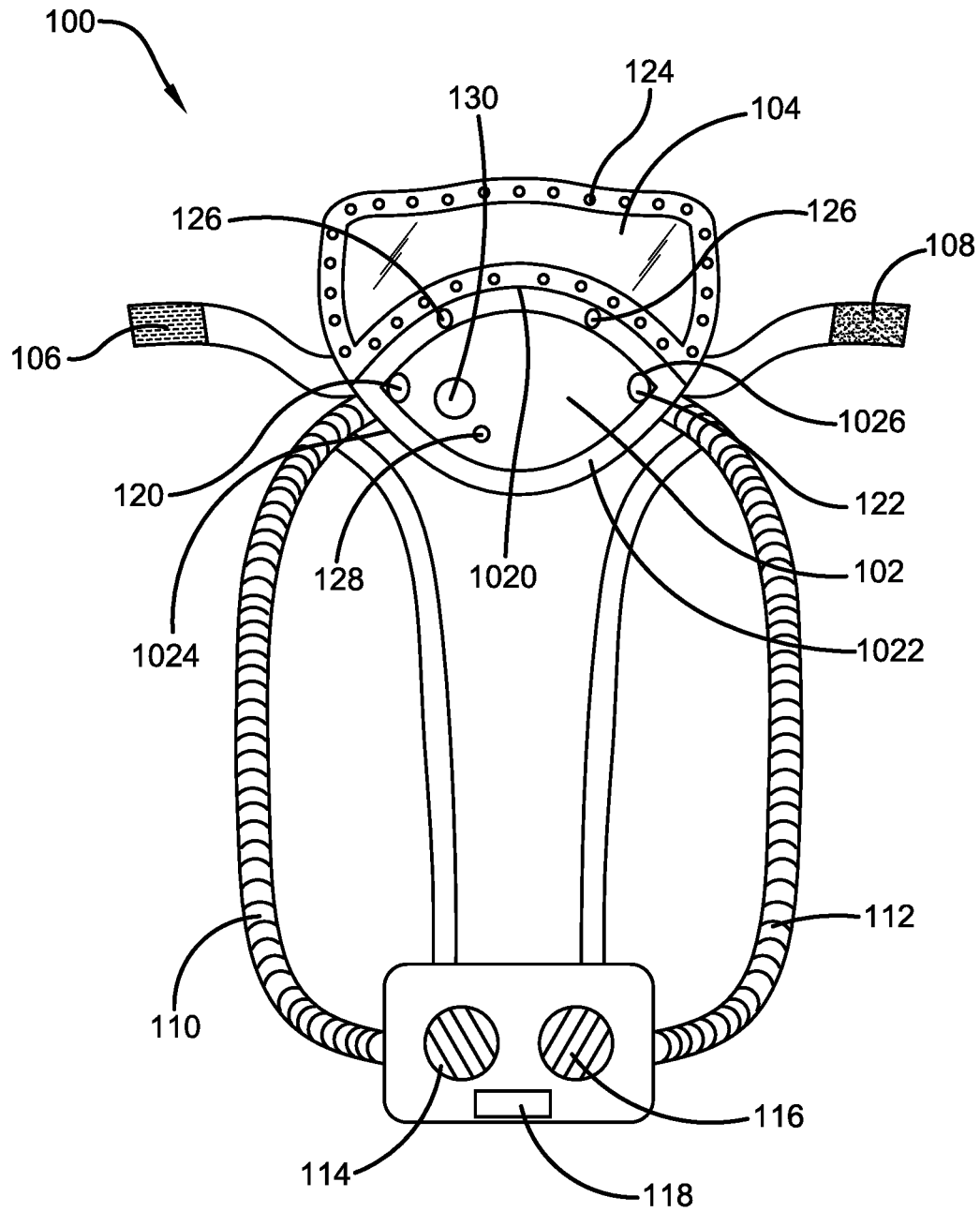
FIG. 1 illustrates a perspective view of one potential embodiment of a personal protective facemask system of the present invention in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long felt need in the art for a protective facemask that provides effective protection against transmission of germs and other harmful pathogens, and therefore prevents the wearer from the spread of infectious diseases. There is also a long felt need in the art for a protective facemask that properly seals the mask over the wearer's face and prevents any germs from travelling inside the mask. Additionally, there is a long felt need in the art for a facemask that provides an enhanced mask-securing mechanism that is comfortable for the wearer and enables the wearer to wear the facemask for long period of time. Moreover, there is a long felt need in the art for a facemask that protects the eyes of the wearer from direct projectiles and contaminants suspended in the air. Further, there is a long felt need in the art for a facemask that eliminates the need to wear facemasks and face shields together. Furthermore, there is a long felt need in the art for a facemask that enables the expressions of the wearer to be clearly visible to others. There is a long felt need in the art for a facemask that enables the wearer to be properly heard by others in order to have an effective communication with others. There is a long felt need in the art for a facemask that prevents the fogging up of glasses and eliminates the need to constantly clear the fogged-up glasses. Finally, there is a long felt need in the art for a comprehensive facemask that maintains a high level of security when in public places with others, while effectively preventing the inhalation and spread of germs, viruses and bacteria.

The present invention, in one potential embodiment, includes a novel personal protective facemask system. The personal protective facemask system includes a transparent facemask, a removable transparent visor, a pair of air tubes for providing fresh air to inhale and removing exhaled air, a microphone disposed on the facemask for capturing wearer's voice, a speaker system disposed on the facemask to amplify wearer's voice for effective communication, a plurality of LEDs, an air filter for filtering air for inhalation and cleaning exhaled air, an air pump for pumping air for inhalation and removing exhaled air and a battery for providing power to the air pump, air filter, microphone, speaker and LEDs.

Referring initially to the drawings, FIG. 1 illustrates a perspective view of one potential embodiment of personal protective facemask system of the present invention in accordance with the disclosed architecture. The personal protective facemask system 100 is designed to deliver clean and filtered air to a wearer of the mask and effectively reduces the chance of inhaling harmful airborne pathogens. More specifically, the facemask system 100 includes a transparent facemask 102 defined by a top side 1020, a bottom side 1022, a right side 1024 and a left side 1026; and, is configured to cover the nose and mouth of a wearer. A removable visor 104 protects the area of the eyes of the wearer. The facemask 102 provides fresh air to the nose and removes exhaled air from nose and mouth. The visor 104 directs fresh air away from the eyes to prohibit eye dehydration and to protect the eyes from pathogens. Both the facemask 102 and the visor 104 can be made from materials that are transparent and flexible hard plastic.

The transparent facemask 102 includes a size and curvature to fit and conform to the nose, jawbone and at least a portion of the neck of the wearer. Further, the facemask 102 seals over the nose, around the jawbone and on a portion of the neck so the mask 102 is not moved by the jawbone when talking. The transparent facemask 102 can be slightly flexible and secures behind the neck of the wearer via a fastening mechanism such as a hook fastener 106 and a loop fastener strap 108. It is contemplated that other type of fasteners such as one or more snap buttons, a clip, or hook/loop fasteners can also be used for securing the facemask 102 behind the neck of the wearer. The transparent facemask 102 on fastening creates a sealed environment for the mouth of the wearer and prevents the nose and mouth of the wearer from contaminated air.

For providing the fresh air for inhalation, an air pump 114 is connected to the facemask 102 through an inlet pipe 110 and an outlet pipe 112. The air pump 114 can be configured to be positioned at one or more of the waist, chest, or back area of the wearer. The air pump 114 uses an integrated battery 118 for pumping the fresh air into the facemask 102. The integrated battery 118 is disposed in a battery pouch and can be positioned near the waist of the wearer. The input air tube or inlet pipe 110 carries fresh air to the facemask 102 and extends from the air pump 114 to the facemask 102. The input air tube 102 carries the fresh air through an opening 120. An output air tube or outlet pipe 112 carries the exhaled air from the facemask 102 through another opening 122 to the external environment, thus eliminating exhaled carbon dioxide and moisture from the facemask 102. The passage of the fresh air and the exhaled air are advantageously separate using the input air tube 110 and the output air tube 112, respectively. A plurality of air filters 116 can be positioned at the waist, chest or back area of the wearer, and can be coupled to the air pump 114 for filtering the air. Also, the air filter 116 can filter out the exhaled air of the wearer before releasing into the environment.

Figure 3:
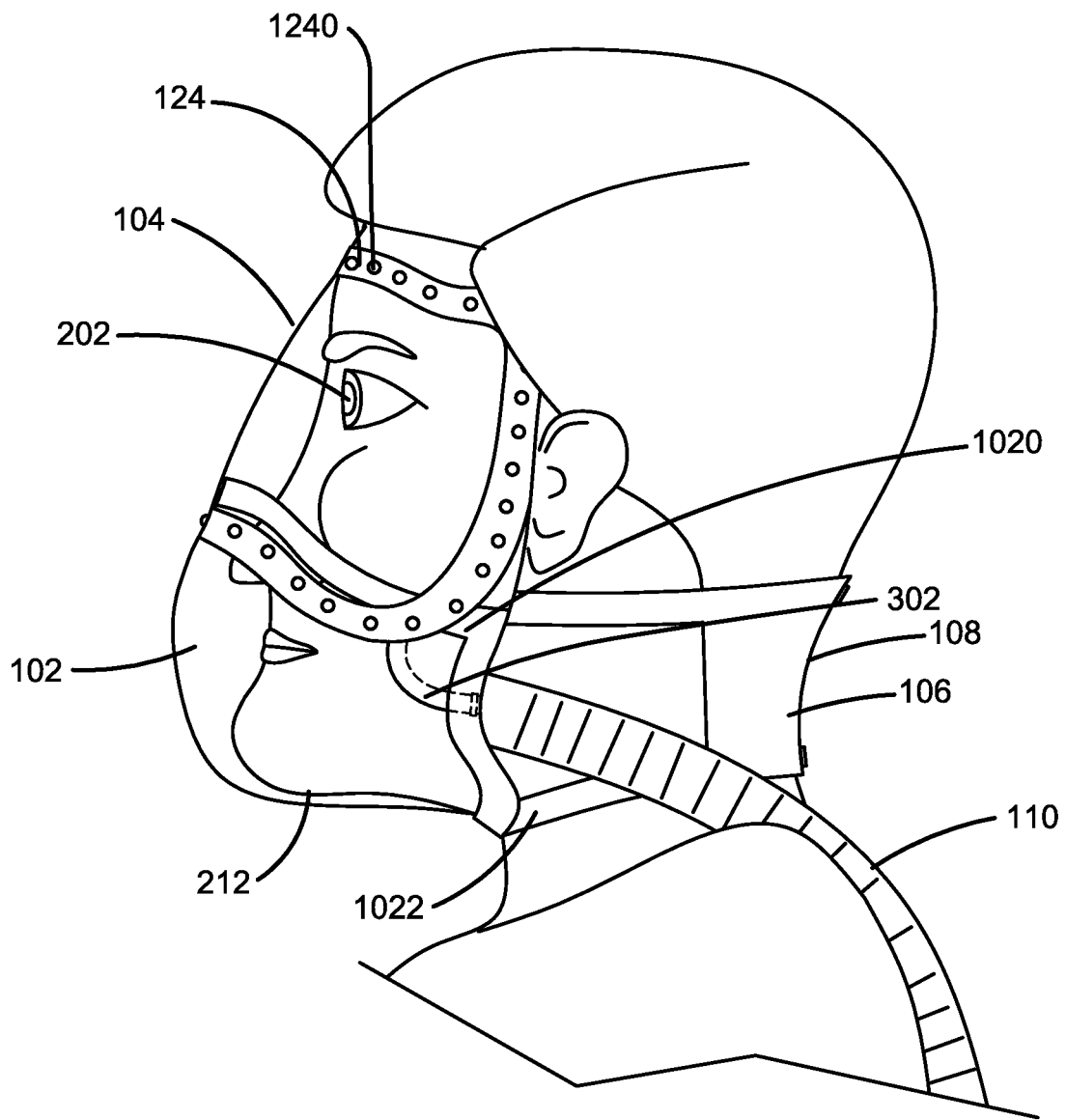
FIG. 3 illustrates a side perspective view of the wearer wearing the personal protective facemask system of the present invention in accordance with the disclosed architecture.

The facemask system 100 includes a selectively-detachable transparent visor 104 configured to protect eyes of the wearer and to keep out harmful vapors, pathogens, and irritants. The transparent nature of the visor 104 does not cause viewing problems for the wearer. The visor 104 includes a perforated air tube 124 generally arranged around the entire perimeter of the visor 104 that provides air received from a connected small air tube (FIG. 3). The small air tube is detachably-connected to the input air tube 110 to intake fresh air and supply same through the perforated air tube 124. The fresh air from the perforated air tube 124 creates a fresh air dam to keep harmful environmental contaminants away from the eyes, and help support cooling of the face. The pores of the perforated air tube 124 push the fresh air at the skin of the wearer and prohibits the eyes from drying out while using the mask visor 104. The visor 104 can be selectively-removed when it is not required by the wearer and the connected small air tube 124 can be detached from the input air tube 110.

A plurality of LEDs 126 can be disposed at the periphery of the facemask 102 and are connected to the integrated battery 118. The LEDs 126 can indicate the status of the air pump 114 and air filters 116. The LEDs 126 can illuminate in a specific color, for example red, indicating that air pump 114, air filters 116, and/or air pressure sensor are malfunctioning, and illuminate in another specific color, for example green, indicating that air pump 114 and air filters 116 are functioning properly. The LEDs 126 are useful in low light areas and also for children and elderly individuals who might not be able to detect that the air pump 114 and air filters 116 are malfunctioning. Additionally, the LEDs 126 can also include white or clear LEDs for projecting illumination in front of the facemask 102.

For enabling effective communication between the wearer and other users, a built-in microphone 128 is provided. The microphone 128 is designed to pick up the voice of the wearer and pass to a speaker system 130. The speaker system 130 amplifies the voice of the wearer, enabling others to clearly hear for effective communication. The microphone 128 can include a noise-cancelling type microphone in order to maintain good voice fidelity. The speaker 130 can be a piezoelectric speaker or a flat panel speaker.

Figure 2:
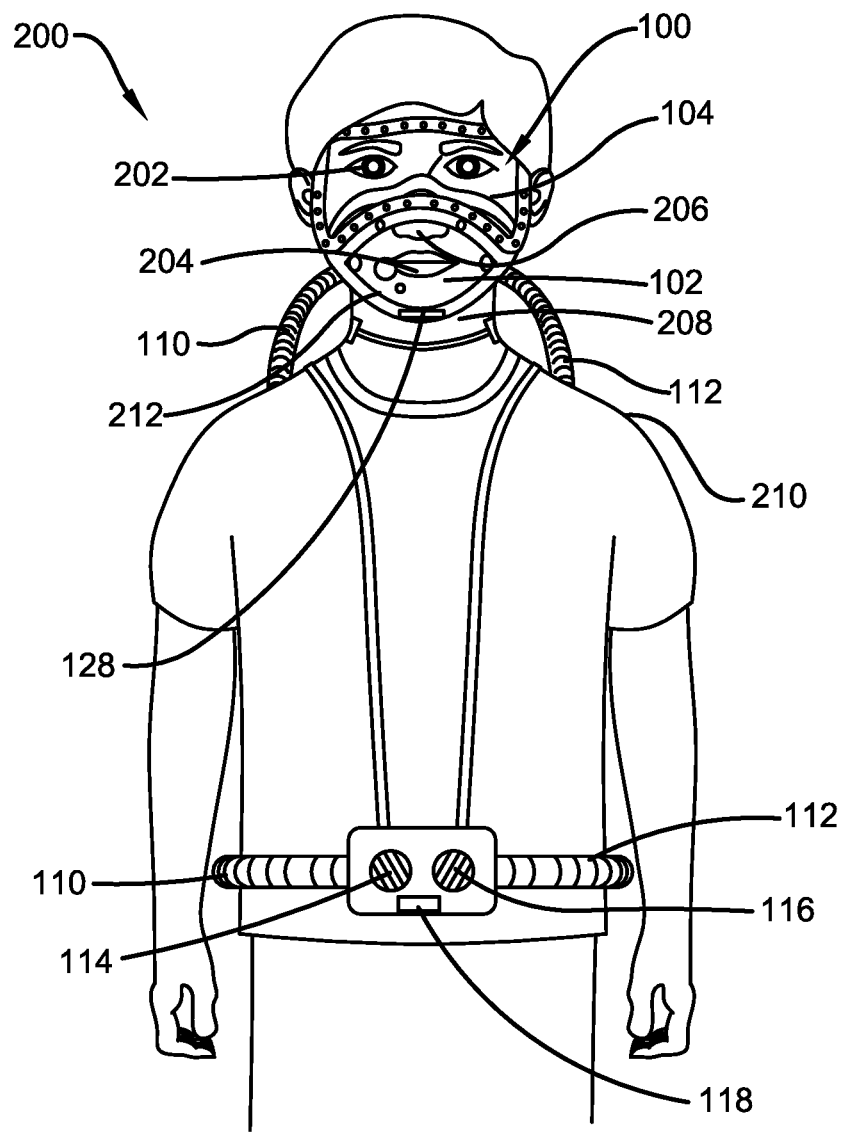
FIG. 2 illustrates a front perspective view of a wearer wearing the personal protective facemask system of the present invention in accordance with the disclosed architecture.

FIG. 2 illustrates a front perspective view of a wearer wearing the personal protective facemask system of the present invention in accordance with the disclosed architecture. As shown, a wearer 200 is wearing the facemask system 100 with the transparent facemask 102 covering mouth 204 (including cheeks), nose 206, and neck 208 of the wearer 200. The inlet pipe 110 and the outlet pipe 112 are connected to the air pump 114 and the air filter 116. The inlet pipe 110 and the outlet pipe 112 can be secured over the shoulder 210 and neck 208 into the air pump system 114 and air filter 116.

As described supra, the transparent facemask 102 includes a size and curvature to fit and conform to the nose 206, jawbone 212 and neck 208 of the wearer 200. Further, the facemask 102 seals over the nose 206, around the jawbone 212 and on a portion of the neck 208, thereby prohibiting unwanted movement of the mask 102 by the jawbone 212 when the wearer 200 is talking. The facemask 102 can include a foam inner lining and/or inflatable membrane to prevent gaps between the facemask and face of the wearer The visor 104 covers the eyes 202 and prohibits direct airflow past, or over, the eye sockets to assist with prohibiting dehydration of the eyes and for keeping the eyes 202 moist. The air pump 114 provides a flow of fresh air and also intakes ambient air for providing to the air filter 116 before providing it into the facemask 102 through the inlet pipe 110. Similarly, the exhaled air from the outlet pipe 112 can be removed to the environment rather than filtering by the filter 116.

FIG. 3 illustrates a side perspective view of the wearer wearing the personal protective facemask system of the present invention in accordance with the disclosed architecture. For providing fresh air to the perforated tube 124 disposed around the periphery of the visor 104, a small air tube 302 is detachably connected to the inlet pipe 110 through a connector 3020. The small air tube 302 transmits a portion of the fresh air carried by the inlet pipe 110. A plurality of perforations 1240 of the perforated tube 124 create a fresh air dam to keep harmful environmental contaminates away from the eyes and help support cooling of the face. It should be appreciated that the perforations 1240 in the perforated tube 124 are aimed directly against the skin and outward in order to prohibit the eyes 202 from receiving air-directed at them which can cause eye dehydration while using the visor 104.

When the visor 104 is removed, the small air tube 302 is detached from the inlet pipe 110. The visor 104 rests on the facemask 102 and does not hinder the view of the wearer 200. The facemask 102, as shown, is sealed by the top side 1020 and the bottom side 1022, along with right and left sides (not shown), and fastened by the fasteners 106, 108. The visor 104 can be stored in the filter/battery pouch.

Figure 4:
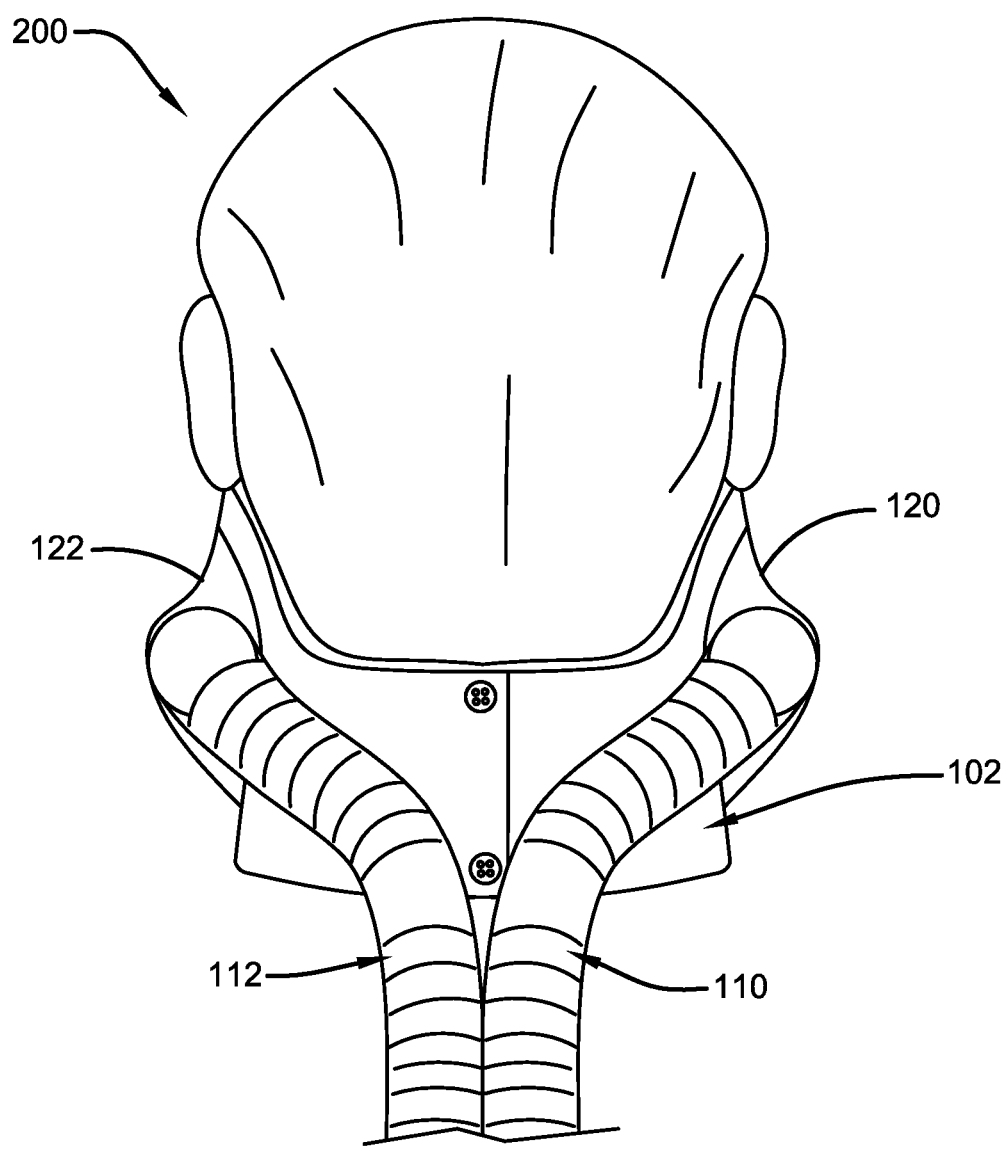
FIG. 4 illustrates a rear close-up view of the wearer wearing the personal protective facemask system of the present invention in accordance with the disclosed architecture.

FIG. 4 illustrates a rear enlarged view of the wearer wearing the personal protective facemask system of the present invention in accordance with the disclosed architecture. As shown, both the inlet pipe 110 and the outlet pipe 112 are flexible and can be shaped and positioned as per the preferences of the wearer 200. The inlet pipe 110 can be attached to the facemask 102 through the opening 120. It should be appreciated that the opening 120 is sized as per the diameter of the inlet pipe 110, and does not allow any foreign particles to enter the facemask 102. Similarly, the outlet pipe 112 is attached to the facemask 102 through the opening 122. The opening 122 is sized as per the diameter of the outlet pipe 112 and prohibits foreign particles from entering the facemask 102.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "personal protective facemask system", "protective facemask system", "facemask system", "transparent facemask system", "full-facemask system" and "modified personal protective facemask system", are interchangeable and refer to the personal protective facemask system 100 of the present invention.

Notwithstanding the forgoing, the personal protective facemask system 100 of the present invention can be of any suitable size and configuration as is known in the art without affecting the overall concept of the invention, provided that it accomplishes the above-stated objectives. One of ordinary skill in the art will appreciate that the size, configuration, and material of the personal protective facemask system 100 as shown in the FIGS. are for illustrative purposes only, and that many other sizes and shapes of the personal protective facemask system 100 are well within the scope of the present disclosure. Although the dimensions of the personal protective facemask system 100 are important design parameters for user convenience, the personal protective facemask system 100 may be of any size that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A personal protective facemask system comprising:
   a transparent facemask including a top side, a bottom side, a right side, and a left side, wherein said transparent facemask seals over a nose, a mouth, a jawbone and a portion of a neck of a wearer;
   a visor for covering the wearer's eyes;
   a fastening mechanism for fastening said transparent facemask to the neck of the wearer;
   an inlet pipe for enabling flow of fresh air to enter said transparent facemask;
   an outlet pipe for enabling flow of exhaled air from said transparent facemask;
   an air pump for moving said fresh air into said transparent facemask and for moving said exhaled air from said transparent facemask;
   an air filter for filtering said flow of fresh air into said transparent facemask;
   a perforated air tube extending around an entire perimeter of the visor in communication with the inlet pipe; and
   an illumination component configured to project illumination in front of the transparent facemask.

2. The protective facemask system of claim 1, wherein said fastening mechanism is a hook and loop fastener.

3. The protective facemask system of claim 1, wherein said transparent facemask is flexible.

4. The protective facemask system of claim 1 further comprising a speaker and a microphone to amplify a voice of said wearer.

5. The protective facemask system of claim 4 further comprising a battery for powering the air pump, the air filter, the microphone and the speaker.

6. The protective facemask system of claim 1, wherein said air filter filters said exhaled air before releasing into an environment.

7. The protective facemask system of claim 1, wherein said visor is selectively detachable from said transparent facemask.

8. A personal protective facemask system comprising:
   a transparent facemask to cover a nose, a mouth, a jawbone, and a portion of a neck of a wearer;
   a visor for covering an eye of the wearer;
   a fastening mechanism for fastening said transparent facemask to a neck of the wearer;
   an inlet pipe for enabling flow of fresh air to enter said transparent facemask;
   an outlet pipe for enabling flow of exhaled air from said transparent facemask;
   an air pump for moving said fresh air into said inlet pipe and to said transparent facemask, and for moving said exhaled air into said outlet pipe and from said transparent facemask;
   an air filter for filtering said flow of fresh air into said transparent facemask;
   a connector element;
   a connecting air tube detachably connected to the inlet pipe via the connector element; and
   a perforated air tube disposed around an entire perimeter of said visor and attached to the connecting air tube opposite the connector element, wherein said perforated air tube receives a portion of said flow of fresh air and transmits said portion of said flow of fresh air to an upper face area of the wearer.

9. The protective facemask system of claim 8, wherein said fastening mechanism is a hook and loop fastener.

10. The protective facemask system of claim 8, wherein said transparent facemask is flexible.

11. The protective facemask system of claim 8 further comprising a speaker and a microphone to amplify a voice of said wearer.

12. The protective facemask system of claim 11 further comprising a battery for powering said air pump, said air filter, said microphone and said speaker.

13. The protective facemask system of claim 8, wherein said air filter filters said exhaled air before releasing into an environment.

14. The protective facemask system of claim 8, wherein said visor selectively detachable from said transparent facemask.

15. A personal protective facemask system comprising:
   a facemask to cover a nose, a mouth, a jawbone, and a portion of a neck of a wearer;
   a visor for covering an eye of the wearer;
   a fastening mechanism for fastening said facemask to a neck of the wearer;
   an inlet pipe for enabling flow of fresh air to enter said facemask;
   an outlet pipe for enabling flow of exhaled air from said facemask;
   an air pump for moving said fresh air into said inlet pipe and to said facemask, and for moving said exhaled air into said outlet pipe and from said facemask;
   an air filter for filtering said flow of fresh air into said facemask;
   a perforated air tube disposed around an entire perimeter of said visor and attached to the inlet pipe via a connecting air tube, wherein said perforated air tube receives a portion of said flow of fresh air and directs said portion of said flow of fresh air to an upper face area away from the eyes of the wearer; and
   a plurality of LEDs disposed around an entire perimeter of said facemask, wherein said LEDs are configured to project illumination in front of the facemask.

16. The protective facemask system of claim 15, wherein said fastening mechanism is a hook and loop fastener.

17. The protective facemask system of claim 15 further comprising a speaker and a microphone to amplify a voice of said wearer.

18. The protective facemask system of claim 17 further comprising a battery for powering said air pump, said air filter, said microphone, and said speaker.

19. The protective facemask system of claim 15, wherein said air filter filters said exhaled air before releasing into an environment.

20. The protective facemask system of claim 15, wherein said visor is selectively detachable from said facemask.

* * * * *